United States Patent [19]

Rubin-Kelley et al.

[11] Patent Number: 5,571,507
[45] Date of Patent: Nov. 5, 1996

[54] METHODS OF TREATING DIABETES

[75] Inventors: Vicki E. Rubin-Kelley; Terry B. Strom, both of Brookline, Mass.; Jean-Francois Bach, Paris, France; Jean C. Nichols, Wayland, Mass.

[73] Assignee: Seragen, Inc., Hopkinton, Mass.

[21] Appl. No.: 840,867

[22] Filed: Feb. 25, 1992

[51] Int. Cl.[6] .................. A61K 45/05; A61K 38/20; C07K 14/55; C07K 7/64
[52] U.S. Cl. .................. 424/85.2; 514/866; 530/321; 530/351
[58] Field of Search .................. 424/85.2; 530/351, 530/321; 514/866

[56] References Cited

U.S. PATENT DOCUMENTS

| 4,468,382 | 8/1984 | Bacha et al. | 424/177 |
| 4,675,382 | 6/1987 | Murphy | 530/350 |
| 5,011,684 | 4/1991 | Strom | 424/85.2 |

FOREIGN PATENT DOCUMENTS 0369316  5/1990  European Pat. Off. .

OTHER PUBLICATIONS

Caillat–Zucman et al. "In Vitro & In Vivo Action of Cyclosporin A on the Induction of Human Interleukin–2 Receptor α & β Chains" Clin. Exp. Immunol 77:184–190 1989.
Kelley et al PNAS, USA vol. 85 (1988) pp. 3980–3984.
Drash et al "Current Issue in Pediatric & Adol. Endo." Pediatric Clinics of No. Amer. vol. 37, No. 6 (Dec. 1990) pp. 1467–1486.
Pacheco–Silva et al Eur. J. Immunol. 1992 vol. 22: 697–702.
Hahn et al Eur. J. Immunol. 1987 vol. 17, pp. 1075–1078.
Feutren et al. "Cyclosporin Increases The Rate & Length of Remissions In Insulin–Dependent Diabetes of Recent Onset" The Lancet Jul. 19 1986 vol. ii 119–123.
Pankewycz et al., Eur. J. Immunol. 21:873–879, 1991.
Bastos et al., The Journal of Immunology 145:3535–3539, 1990.
Drash et al., Pediatric Clinics of North Amer. 37:1467–1487, 1990.
Williams et al., The Journal of Biological Chemistry 265:20673–20677, 1990.
Byers et al., Blood 75:1426–1432, 1990.
Waters et al., Eur. J. Immunol. 20:785–791, 1990.
Pankewycz et al., Transplantation 47:318–322, 1989.
Kirkman et al., Transplantation 47:327–330, 1989.
Haskins et al., Proc. Natl. Acad. Sci. USA 86:8000–8004, 1989.
Kiyokawa et al., Cancer Research 49:4042–4046, 1989.
Collins et al., Proc. Natl. Acad. Sci. USA 85:7709–7713, 1988.
Kelley et al., Proc. Natl. Acad. Sci. USA 85:3980–3984, 1988.
Smith, Science 240:1169–1176, 1988.
Kelley et al., The Journal of Immunology 140:59–61, 1988.
Williams et al., Nucleic Acids Research 16:10453–10467, 1988.
Pankewycz et al., Journal of Autoimmunity 1:119–130, 1988.
Brandhuber et al., Science 238:1707–0709, 1987.
Shizuru et al., Science 237:278–280, 1987.
Calderwood et al., Proc. Natl. Acad. Sci. USA 84:4364–4368, 1987.
Ju et al., The Journal of Biological Chemistry 262:5723–5731, 1987.
Robb et al., Proc. Natl. Acad. Sci. USA 84:2002–2006, 1987.
Hwang et al., Cell 48:129–136, 1987.
Smith, J. Exp. Med. 165:223–238, 1987.
Williams et al., Protein Engineering 1:493–498, 1987.
Tsudo et al., Proc. Natl. Acad. Sci. USA 83:9694–9698, 1986.
Cohen et al., Science 234:349–352, 1986.
Colombatti et al., The Journal of Biological Chemistry 261:3030–3035, 1986.
Hoch et al., Proc. Natl. Acad. Sci. USA 82:1692–1696, 1985.
Gray et al., Proc. Natl. Acad. Sci. USA 81:2645–2649, 1984.
Stiller et al., Science 223:1362–1367, 1984.
Deleers et al., FEBS 160:82–86, 1983.
Taniguchi et al., Nature 302:305–310, 1983.
Maassen et al., Eur. J. Biochem 134:327–330, 1983.
Makino et al., Exp. Anim. 29:1–13, 1980.
Bach, M.D., D.Sc. et al.; The Prospects of Immunosuppression in Type I Diabetes; 1988; Year Book Medical Publishers, Inc.
Rubenstein, Arthur H. et al.; Immunosuppression in the Treatment of Insulin–Dependent (Type 1) Diabetes; Feb. 27, 1987; The Lancet Ltd, 1987.
Grant, Adrian et al.; Cerebral Palsy Among Children Born During The Dublin Randomised Trial of Intrapartum Monitoring; Nov. 25, 1989; The Lancet Ltd, 1989.

*Primary Examiner*—George C. Elliott
*Assistant Examiner*—Nancy J. Degen
*Attorney, Agent, or Firm*—Fish & Richardson, P.C.

[57] ABSTRACT

A method of treating a patient with diabetes involving administering to the patient a hybrid molecule which contains a cytotoxin covalently joined to interleukin-2 which is capable of binding to interleukin-2 receptor on a cell that contributes to the disease state of the cell and decreasing the viability of that cell.

14 Claims, 1 Drawing Sheet

METHODS OF TREATING DIABETES

BACKGROUND OF THE INVENTION

The field of the invention is diabetes.

Diabetes mellitus is a prevalent and degenerative disease characterized by insulin deficiency, which prevents normal regulation of blood glucose levels leading to hyperglycemia and ketoacidosis.

Insulin promotes glucose utilization, protein synthesis, formation and storage of neutral lipids, and the growth of some cell types. Insulin is produced by the β cells within the islets of Langerhans of the pancreas.

Some individuals with diabetes are not dependent upon the administration of exogenous insulin, other individuals are completely dependent upon exogenously administered insulin. Insulin-dependence is related to the degree of destruction of the β islet cells. Diabetic patients that are not insulin-dependent can be diagnosed as having diabetes if they exhibit some of the symptoms of the disease, e.g., hyperglycemia, and have antibodies to insulin or islet cells, or both. Such patients may progress to full-blown insulin-dependent diabetes mellitus if they are not treated.

Insulin-dependent diabetes mellitus (IDDM) is a T cell dependent autoimmune disease. Activated T cells selectively target insulin producing beta cells and mediate their destruction. In the most severe form of diabetes, the autoimmune reaction causes complete destruction of β cells, resulting in an absolute lack of insulin production in the individual.

The importance of T cells in human diabetogenic autoimmunity is emphasized by the ability of cyclosporine A to cause remission in new onset IDDM (Stiller et al., 1984, *Science* 223:1362). However, cyclosporin A-induced remissions have not been proven to be permanent, and the chronically administered high doses of cyclosporin A required to maintain a remission are associated with nephrotoxicity. Thus, cyclosporin A is an unlikely candidate for general clinical use (Drash et al., 1990, in Pediatric Clinics of North America: Current Issues in Pediatric and Adolescent Endocrinology 37:6).

Studies in the non-obese diabetic mouse (NOD) indicate that the disease in mice is similar to IDDM in humans (Makino et al., 1980, Exp. Anim. 29:1). Anti-T cell monoclonal antibodies (anti-Thy 1.2 or anti-CD4) prevent disease in NOD mice (Harada and Makino, 1986, Exp. Anim. 35:539; Shizura et al., 1988, *Science* 250:659) and anti-CD 25 has been shown to prevent insulitis in NOD mice (Kelley et al., 1988, *J. Immunol.* 140:59). However, the action of anti-CD25 antibody was subsequently shown to be blocked by anti-idiotypic antibodies which had been generated in NOD mice (Pankewycz et al., 1988, *J. Autoimmunity* 1:119). T cell clones obtained from the islets of prediabetic mice with insulitis precipitate diabetes when transferred into prediabetic NOD mice (Pankewycz et al., 1991, *Eur. J. Immunol.* 21:873; Haskins et al., 1989, *Proc. Natl. Acad. Sci.* 86:8000).

SUMMARY OF THE INVENTION

The invention features a method of treating a patient with diabetes which involves administering to the patient a hybrid molecule which contains a cytotoxin covalently fused to interleukin-2, or a receptor-binding portion thereof. The molecule is capable of binding to a cell which contributes to the disease state of the patient and contains a high affinity interleukin-2 receptor. The molecule is further capable of decreasing the viability of the cell, preferably by killing the cell.

The cytotoxin molecule is preferably a fragment of a peptide toxin which is enzymatically active but which does not possess generalized eukaryotic receptor binding activity.

Preferably, the fragment of peptide toxin can be fragment A of diphtheria toxin and enough of fragment B of diphtheria toxin to form a pore in a cell membrane.

The hybrid molecule is most preferably $DAB_{486}IL$-2 or $DAB_{389}IL$-2.

The term diabetes includes patients that are insulin-dependent, that are not dependent on exogenously administered insulin but that exhibit some of the symptoms of diabetes, for example, hyperglycemia, and that have antibodies to either islet cells, insulin, or both. Patients that are not insulin-dependent eventually become dependent as the disease progresses. Accordingly, the invention features methods for the treatment of patients with each of the levels of diabetes as defined above.

The invention also features a method of treating a patient with diabetes wherein there is administered a hybrid cytotoxin IL-2 molecule and cyclosporin A. Cyclosporin A is administered either in conjunction with the hybrid molecule, or is administered after the diabetic condition of the patient has substantially improved as a result of treatment with the hybrid molecule. In this method of treatment, cyclosporin A can be administered at dosage levels that are effective and yet non-toxic compared to the levels required to treat a patient that does not receive the hybrid molecule.

Other features and advantages of the invention will be apparent from the following detailed description, and from the claims.

DETAILED DESCRIPTION

INTERLEUKIN-2 AS A TARGETING AGENT

Figure 1A:
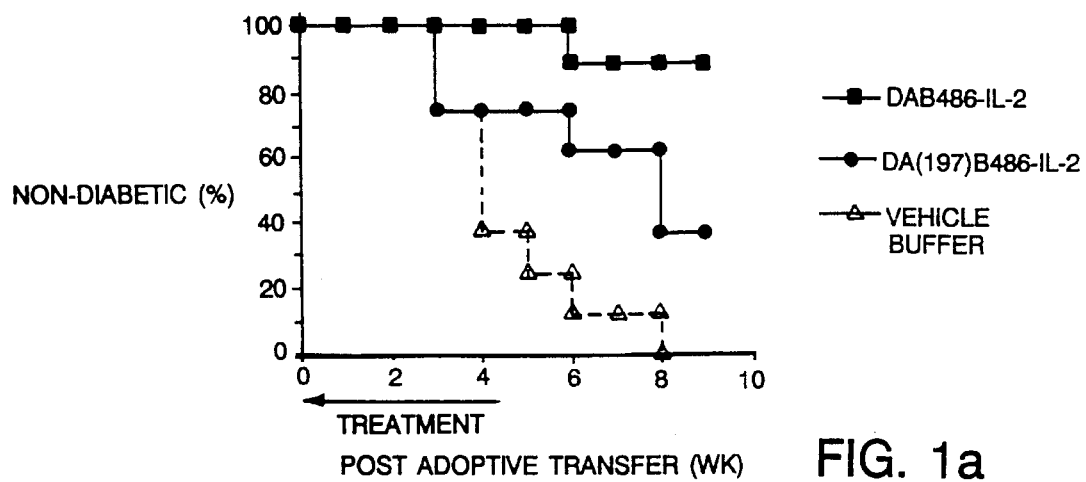
FIG. 1A and 1B are graphical representation of the effect of $DAB_{486}IL$-2 and $DA(197)B_{486}IL$-2 on the acquisition of diabetes. Prediabetic NOD mice were irradiated (1,000 rad) and injected i.v. with $2 \times 10^7$ mononuclear spleen cells from diabetic NOD mice. a) Mice were injected daily with vehicle buffer (n=8), 10 μg of $DA(197)B_{486}IL$-2 (n=8) or 10 μg of $DAB_{486}IL$-2 (n=9) during 4 weeks after adoptive transfer. b) Mice were injected daily with vehicle buffer (n=8), or 5 μg of $DAB_{486}IL$-2 (n=8) during 4 weeks after adoptive transfer.

Interleukin-2 (IL-2) or any IL-2 receptor binding derivative thereof can be used as a targeting agent for a cytotoxin. The DNA and amino acid sequences of IL-2 are known (Tadatsugu et al., *Nature* 302:305, 1983), and its structure has been predicted by x-ray crystallography (Brandhuber et al., *Science* 238:1707, 1987). Analysis of genetically engineered variants of IL-2 has provided some information concerning which residues are important for IL-2R binding (Collins et al., *Proc. Natl. Acad. Sci.* USA 85:7709, 1988) and bioactivity (Cohen et al. *Science* 234:349, 1989; Collins et al., supra). Variants of IL-2 which are useful in the invention include deletion mutants (Genbauffe et al., U.S. Ser. No. 388,557, hereby incorporated by reference) which lack one or more amino acid residues in the region between residue 74 and residue 79 (numbering according to Williams et al., Nucl. Acids Res. 16:1045, 1988). These mutants effectively target toxins to IL-2R-bearing cells (Genbauffe et al., supra). Generally, IL-2 variants useful for targeting a cytotoxin must efficiently bind IL-2R and be endocytosed. The ability of various derivatives to bind to the IL-2 receptor can be tested with an IL-2R binding assay described below.

In designing molecules targeted to cells bearing the IL-2 receptor it must be recognized that the IL-2 receptor, like other receptors, has several forms; and it may be desirable to target cells bearing one form and not another. The human interleukin-2 receptor has a high-, an intermediate-, and a low-affinity form. The high affinity receptor has an apparent $K_d$ of ~$10^{-10}$M and is composed of two subunits, p55 and p75 (also called p70). When expressed on the cell surface, both the p75 and p55 subunits are capable of binding IL-2. The p75 subunit corresponds to the intermediate affinity receptor ($K_d$~$8.2\times10^{-10}$M), and p55 subunit corresponds to the low affinity receptor ($K_d$~$1$–$3\times10^{-8}$M). The p75 subunit is expressed on the surface of resting T cells, natural killer cells, monocytes/macrophages, and lymphokine-activated killer (LAK) cell precursors, while the high affinity receptor is expressed on activated T- and B-cells.

In the method of the invention it may be desirable to target only cells bearing the high affinity receptor. In these circumstances, useful molecules will eliminate or neutralize cells bearing the high affinity IL-2 receptor at a concentration which leaves cells bearing the intermediate or low affinity receptor largely unaffected. When the molecule, like IL-2 itself, has affinity for all three classes of IL-2 receptor, selectivity can be accomplished by administering the molecule at a concentration which does not permit significant binding to cells bearing lower affinity receptors. A hybrid molecule may have altered receptor affinities compared to IL-2. Such hybrid molecules may be more or less selective for cells bearing the high affinity IL-2 receptor. For example, cells bearing the high-affinity receptor are 500–1000 times more sensitive to $DAB_{486}IL$-2, a fusion protein consisting of part of diphtheria toxin and part of IL-2, than are cells bearing the intermediate-affinity receptor (Waters et al., *Eur. J. Immunol.* 20:785, 1990).

A cytotoxin can be attached to an IL-2 derivative in a number of ways. Preferably, an IL-2/toxin hybrid is a hybrid protein produced by the expression of a fused gene. Alternatively, the cytotoxin and the IL-2 derivative can be produced separately and later coupled by means of a nonpeptide covalent bond. Linkage methods are described below.

Useful cytotoxins are preferably significantly cytotoxic only when present intracellularly and are substantially excluded from any given cell in the absence of a targeting domain. Peptide toxins fulfill both of these criteria and are readily incorporated into hybrid molecules. A mixed cytotoxin, a cytotoxin composed of all or part of two or more toxins, can also be used. Several useful toxins are described in more detail below.

Toxins

The toxin molecules useful in the method of the invention are preferably toxins, such as peptide toxins, which are significantly cytotoxic only when present intracellularly. Of course, under these circumstances the molecule must be able to enter a cell bearing the targeted receptor. This ability depends on the nature of the molecule and the nature of the cell receptor. For example, cell receptors which naturally allow uptake of a ligand are likely to provide a means for a molecule which includes a toxin to enter a cell bearing that receptor. The peptide toxin useful in the methods of the invention is fused to an IL-2 binding domain by producing a recombinant DNA molecule which encodes a hybrid protein molecule. Such an approach ensures consistency of composition.

Many peptide toxins have a generalized eukaryotic receptor binding domain; in these instances the toxin must be modified to prevent intoxication of non-receptor bearing cells. Any such modifications must be made in a manner which preserves the cytotoxic functions of the molecule (see U.S. Department of Health and Human Services, U.S. Ser. No. 401,412). Potentially useful toxins include, but are not limited to: cholera toxin, ricin, 0-Shiga-like toxin (SLT-I, SLT-II, SLT II$_v$), LT toxin, C3 toxin, Shiga toxin, pertussis toxin, tetanus toxin, Pseudomonas exotoxin, alorin, saporin, modeccin, and gelanin.

Mixed Toxins

The cytotoxic portion of some molecules useful in the invention can be provided by a mixed toxin molecule. A mixed toxin molecule is a molecule derived from two different polypeptide toxins. Generally, as discussed above in connection with diphtheria toxin, polypeptide toxins have, in addition to the domain responsible for generalized eukaryotic cell binding, an enzymatically active domain and a translocation domain. The binding and translocation domains are required for cell recognition and toxin entry respectively. The enzymatically active domain is the domain responsible for cytotoxic activity once the molecule is inside a cell.

Naturally-occurring proteins which are known to have a translocation domain include diphtheria toxin, Pseudomonas exotoxin A, and possibly other peptide toxins. The translocation domains of diphtheria toxin and Pseudomonas exotoxin A are well characterized (see, e.g., Hoch et al., *Proc. Natl. Acad. Sci. USA* 82:1692, 1985; Colombatti et al., *J. Biol. Chem.* 261:3030, 1986; and Deleers et al., *FEBS Lett.* 160:82, 1983), and the existence and location of such a domain in other molecules may be determined by methods such as those employed by Hwang et al. *Cell* 48:129, 1987); and Gray et al. *Proc. Natl. Acad. Sci. USA* 81:2645, 1984).

One useful IL-2/mixed toxin hybrid molecule is formed by fusing the enzymatically active A subunit of E. coli Shiga-like toxin (Calderwood et al., *Proc. Natl. Acad. Sci. USA* 84:4364, 1987) to the translocation domain (amino acid residues 202 through 460) of diphtheria toxin, and to IL-2. This three-part hybrid molecule, SLT-A/DTB'/IL-2, is useful in the method of the invention in the same way as $DAB_{486}IL$-2 described above. The IL-2 portion of the three-part hybrid causes the molecule to attach specifically to IL-2R-bearing cells, and the diphtheria toxin translocation portion acts to insert the enzymatically active A subunit of the Shiga-like toxin into the targeted cell. The enzymatically active portion of Shiga-like toxin, like diphtheria toxin, acts on the protein synthesis machinery of the cell to prevent protein synthesis, thus killing the cell. The difference between these two types of hybrid toxins is the nature of their enzymatic activities: the enzymatic portion of $DAB_{486}IL$-2 catalyzes the ADP-ribosylation by nicotinamide adenine dinucleotide of Elongation Factor 2, thereby inactivating this factor which is necessary for protein synthesis, while the enzymatic portion of SLT-A/DTB'/IL-2 is a ribonuclease capable of cleaving ribosomal RNA at a critical site, thereby inactivating the ribosome. SLT-A/DTB'/IL-2 hybrid would therefore be useful as a treatment for the same indications as $DAB_{486}$IL-2, and could be substituted or used in conjunction with it if, for example, a patient's activated T-cells develop a resistance to $DAB_{486}$IL-2.

Linkage of Toxins to Binding Ligands

The binding ligand and the cytotoxin of useful hybrid molecules can be linked in several ways. If the hybrid molecule is produced by expression of a fused gene, a peptide bond serves as the link between the cytotoxin and the binding ligand. Alternatively, the toxin and the binding ligand can be produced separately and later coupled by means of a non-peptide covalent bond.

For example, the covalent linkage may take the form of a disulfide bond. In this case, if the binding ligand is a protein, e.g., IL-2, the DNA encoding IL-2 can be engineered to contain an extra cysteine codon as described in Murphy et al. U.S. Ser. No. 313,599, hereby incorporated by reference. The cysteine must be positioned so as to not interfere with the IL-2R binding activity of the molecule. For example, the cysteine codon can be inserted just upstream of the DNA encoding $Pro_2$ of the mature form of IL-2. The toxin molecule must be derivatized with a sulfhydryl group reactive with the cysteine the modified IL-2. In the case of a peptide toxin this can be accomplished by inserting a cysteine codon into the DNA sequence encoding the toxin. Alternatively, a sulfhydryl group, either by itself or as part of a cysteine residue, can be introduced using solid phase polypeptide techniques. For example, the introduction of sulfhydryl groups into peptides is described by Hiskey (Peptides 3:137, 1981). Derivatization can also be carried out according to the method described for the derivatization of a peptide hormone in Bacha et al. U.S. Pat. No. 4,468,382, hereby incorporated by reference. The introduction of sulfhydryl groups into proteins is described in Maasen et al. (*Eur. J. Biochem.* 134:32, 1983). Once the correct sulfhydryl groups are present, the cytotoxin and IL-2R binding ligand are purified, both sulfur groups are reduced; cytotoxin and ligand are mixed;, (in a ratio of about 1:5 to 1:20) and disulfide bond formation is allowed to proceed to completion (generally 20 to 30 minutes) at room temperature. The mixture is then dialyzed against phosphate buffered saline to remove unreacted ligand and toxin molecules. Sephadex chromatography or the like is then carried out to separate on the basis of size the desired toxin-ligand conjugates from toxin-toxin and ligand-ligand conjugates.

Assays for IL-2 Receptor Binding

The IL-2R binding ability of various molecules can be measured using an IL-2R assay for high affinity (Ju et al., *J. Biol. Chem.* 262:5723, 1987) or intermediate affinity receptors (Rob et al., *Proc. Natl. Acad. Sci.* USA 84:2002, 1987).

Assays for Toxicity

Molecules of the invention can be screened for the ability to decrease viability of cells bearing the targeted receptor by means of assays such as those described below.

Toxicity towards IL-2R bearing cells can be tested as follows. Cultured HUT 102/6TG (Tsudo et al., *Proc. Natl. Acad. Sci.* USA 83:9694, 1986) or YT2C2 (Teshigiwari et al., *J. Exp. Med.* 165:223, 1987) cells are maintained in RPMI 1640 medium (Gibco, Grand Island, N.Y.) supplemented with 25 mM HEPES (pH 7.4), 2 mM 1-glutamine, 100 U/ml penicillin, 100 μg/ml streptomycin, and 10% fetal calf serum (Hazelton, Lenexa, Kans.). Cells are seeded in 96-well V-bottomed plates (Linbro-Flow Laboratories, McLean, Va.) at a concentration of $1\times10^5$ per well in complete medium. Putative toxins are added to varying concentrations ($10^{-12}$M to $10^{-6}$M) and the cultures are incubated for 18 hrs. at 37° C. in a 5% $CO_2$ atmosphere. Following incubation, the plates are centrifuged for 5 min. at 170×g, and the medium removed and replaced with 100 μl leucine-free medium (MEM, Gibco) containing 8 μCi/ml ($^3$H-leucine; New England Nuclear, Boston, Mass.) After an additional 90 min at 37° C. the plates are centrifuged for 5 min. at 170×g, the medium is removed, and the cells are collected on glass fiber filters using a cell harvester (Skatron, Sterling, Va.). Filters are washed, dried, and counted according to standard methods. Cells cultured with medium alone serve as the control.

Diphtheria Toxin-based Molecules

Diphtheria toxin can be used to produce molecules useful in the methods of the invention. Diphtheria toxin, whose sequence is known, is described in detail in Murphy U.S. Pat. No. 4,675,382, hereby incorporated by reference. The natural diphtheria toxin molecule secreted by *Corynebacterium diphtheriae* consists of several functional domains which can be characterized, starting at the amino terminal end of the molecule, as enzymatically-active Fragment A (amino acids $Gly_1$- $Arg_{193}$) and Fragment B (amino acids $Ser_{194}$-$Ser_{535}$), which includes a translocation domain and a generalized cell binding domain (amino acid residues 475 through 535).

The process by which diphtheria toxin intoxicates sensitive eukaryotic cells involves at least the following steps: (i) the binding domain of diphtheria toxin binds to specific receptors on the surface of a sensitive cell; (ii) while bound to its receptor, the toxin molecule is internalized into an endocytic vesicle; (iii) either prior to internalization, or within the endocytic vesicle, the toxin molecule undergoes a proteolytic cleavage between fragments A and B; (iv) as the pH of the endocytic vesicle decreases to below 6, the toxin crosses the endosomal membrane, facilitating the delivery of Fragment A into the cytosol; (v) the catalytic activity of Fragment A (i.e., the nicotinamide adenine dinucleotide-dependent adenosine diphosphate (ADP) ribosylation of the eukaryotic protein synthesis factor termed "Elongation Factor 2") causes the death of the intoxicated cell. It is apparent that a single molecule of Fragment A introduced into the cytosol is sufficient to block down the cell's protein synthesis machinery and kill the cell. The mechanism of cell killing by Pseudomonas exotoxin A, and possibly by certain other naturally-occurring toxins, is very similar.

$DAB_{486}$IL-2, a fusion protein in which the receptor binding domain of diphtheria toxin has been replaced by a portion of human IL-2 (Williams et al., *J. Biol. Chem.* 35:20673, 1990; see also Williams et al., *Protein Eng.* 1:493, 1987), is an example of a molecule useful in the method of the invention. This molecule selectively kills IL-2R-expressing tumor cells and lymphocytes (Waters et al., *Eur. J. Immunol.* 20:785, 1990; Kiyokawa et al., *Cancer Res.* 49:4042, 1989). Because of its ability to kill activated lymphocytes, $DAB_{486}$IL-2 has been used to control graft rejection (Pankewycz et al., *Transplantation* 47:318, 1989; Kickman et al., *Transplantation* 47:327, 1989) and to treat certain autoimmune disorders (Forte et al., 2nd International Symposium on Immunotoxins, 1990).

$DAB_{486}IL-2$ is a chimeric molecule consisting of Met followed by amino acid residues 1 through 485 of the mature diphtheria toxin fused to amino acid residues 2 through 133 of IL-2. Thus, $DAB_{486}IL-2$ includes all of diphtheria toxin fragment A, which encodes the enzymatically active portion of the molecule, and a portion of fragment B. The portion of fragment B present in $DAB_{486}IL-2$ does not include the generalized receptor binding domain but does include the translocation domain which facilitates delivery of the enzymatically active portion into the cytosol.

A second molecule useful in the invention is $DAB_{389}IL-2$, which is similar to $DAB_{486}IL-2$ except that it contains 97 amino acids less than $DAB_{486}IL-2$.

Preparation of $DAB_{486}IL-2$ and $DAB_{389}IL-2$ $DAB_{486}IL-2$ and $DAB_{389}IL-2$ are produced and purified as described in U.S. patent application Ser. No. 07/537,430, filed on Jun. 13, 1990, and corresponding PCT patent application Ser. No. 91/01282. $DAB_{389}-IL-2$ was constructed by removing a 309 bp HpaII-SphI restriction fragment from pDW24 and replacing it with oligonucleotide linker 261/274 to generate plasmid pDW27. This linker restores fragment B sequences from Pro383 to Thr387, and allows for in-frame fusion to IL-2 sequences at this position. Thus, in $DAB_{389}-IL-2$ the 97 amino acids between Thr387 and His485 have been deleted.

```
DAB389-IL-2  274  5'-CG GGT CAC AAA ACG CAT G-3'
             261     CCA GTG TTT TGC
                  1/2 HpaII              1/2 SphI
```

IL-2 Toxin Treatment Blocks Diabetogenic Autoimmunity in NOD Mice

High affinity interleukin-2 receptor (IL-2R) is a feature of recently activated T cells and is not detected on resting T cells (Smith, 1988, *Science* 240:1169; Teshigawara et al., *J. Exp. Med.* 165:223). An ideal therapeutic for diabetes should rapidly and selectively destroy the activated, autoaggressive T cells. It has been demonstrated that diabetogenic cells express IL-2R in vivo (Pankewycz et al., 1991, *Eur. J. Immunol.* 21:873). The data described below demonstrates that specific elimination of IL-2R+ T-cells aborts the diabetogenic process. In summary, NOD mice were treated with the IL-2 fusion toxin ($DAB_{486}IL-2$). $DAB_{486}IL-2$ selectively binds to the high affinity IL-2-R heterodimer (Waters et al., 1990, *Eur. J. Immunol.* 20:785). This fusion toxin exerts potent immunosuppression in vivo by preventing delayed type hypersensitivity (Kelley et al., 1988, *Proc. Natl. Acad. Sci. USA* 85:3980) via selective targeting of antigen activated T-cells (Bastos et al., 1990, *J. Immunol.* 145:3535) and by prolonging engraftment, often indefinitely, of allogeneic heart or islet grafts (Kirkman et al., 1989, *Transplantation* 47:327; Pankewyzc et al., 1989, *Transplantation* 47:318). The data described below demonstrate that $DAB_{486}IL-2$ treatment inhibits diabetogenic autoimmunity in NOD mice. In addition, diabetic NOD mice treated with $DAB_{486}IL-2$ do not bear spleen cells that transfer IDDM into prediabetic NOD mice.

Materials and Methods

As described above, $DAB_{486}IL-2$ is the product of a fusion gene in which the human IL-2 sequence replaces the codons for the receptor-binding domain of diphtheria toxin (Williams et al., 1987, *Protein Eng.* 1:493). $DA(197)B_{486}IL-2$, is a mutant form of $DAB_{486}IL-2$ in which a single amino acid change at position 52 (glycine to glutamic acid) results in a loss of ADP-ribosyltransferase activity. $DA(197)B_{486}IL-2$ was used as a control molecule. These proteins were purified from cellular extracts of Escherichia coli. They were free of contamination by endotoxins, were suspended in a vehicle buffer (Tris Buffer Saline), pH 7.9, and were aliquoted at concentrations of 10, 5 and 1 µg/ml. Recombinant human IL-2 was purchased from Biogen Inc. (Cambridge, Mass.).

Adoptive Transfer of Diabetes

Two month-old, female NOD mice (Brigham and Women's Hospital; original breeding pairs Jackson Laboratory, Bar Harbor Me.) were lethally irradiated (1,000 rads) and injected intravenously within 4 hours of irradiation with 1.5 to $2.0 \times 10^7$ mononuclear spleen cells harvested from spontaneously diabetic NOD mice that had blood glucose levels of > 300 md/dl. Administration of this number of cells uniformly induced diabetes in 2 month old female NOD mice by 21 days.

Mice were treated subcutaneously with 10 µg/d, 5 µg/d, or 1 µg/d, of $DAB_{486}IL-2$ or with 10 µg/d of $DA(197)B_{486}IL-2$ or with 0.1 ml of the vehicle buffer. To assess the ability of $DAB_{486}IL-2$ to prevent diabetogenic autoimmunity, some diabetic NOD were treated with 10 µg/d $DAB_{486}IL-2$ for 1 week. Spleen cells from treated or control mice were adoptively transferred to lethally irradiated 2 month old prediabetic NOD which received no further treatment.

Results $DAB_{486}IL-2$ protects NOD mice from adoptively transferred diabetes $DAB_{486}IL-2$ treatment administered subcutaneously prevents diabetes in pre-diabetic NOD mice adoptively transferred with mononuclear spleen cells from diabetic NOD mice. Each of 8 NOD mice injected with a vehicle buffer became diabetic (measured as a sustained blood glucose level of > 200 mg/dl, i.e., three standard deviations above the mean of the blood glucose level measured in prediabetic NOD mice) within 8 weeks of adoptive transfer. By comparison, only 1/9 mice injected with 10 µg/d of $DAB_{486}IL-2$ became diabetic (p<0.001) in this period, while 4/8 of those mice injected with $DA(197)B_{486}IL-2$ remained euglycemic (p<0,007) in the same period (FIG. 1a). Histologic examination of the group of mice receiving $DAB_{486}IL-2$ sacrificed at 9 weeks, who remained normoglycemic after receiving diabetogenic T cells, had minimal numbers of mononuclear infiltrates within islets (1.2±0.6, n=8). By comparison, 5/8 vehicle control treated mice who became diabetic by 4 weeks were already dead and there were few islets remaining in the 3 diabetic sacrificed mice. Unexpectedly, when $DAB_{486}IL-2$ or $DAB_{389}$ IL-2 was administered intravenously to prediabetic NOD mice that had received mononuclear spleen cells from diabetic NOD mice, neither compound had any impact on the diabetic process.

In a second set of experiments designed to determine if $DAB_{486}IL-2$ targets diabetogenic cells, spleen cells transferred from diabetic donor NOD mice injected with $DAB_{486}IL-2$ were transferred into recipients and were found to be incapable of inducing diabetes within 8 weeks after adoptive transfer (0/4 mice). By comparison, spleen cells from untreated diabetic donor NOD mice induced diabetes in 8/9 animals within this same period (Table 2). Therefore, elimination of IL-2R bearing cells from diabetic donor spleen cells in vivo results in at least partial elimination of autoimmune diabetogenic T-cells.

Figure 1B:
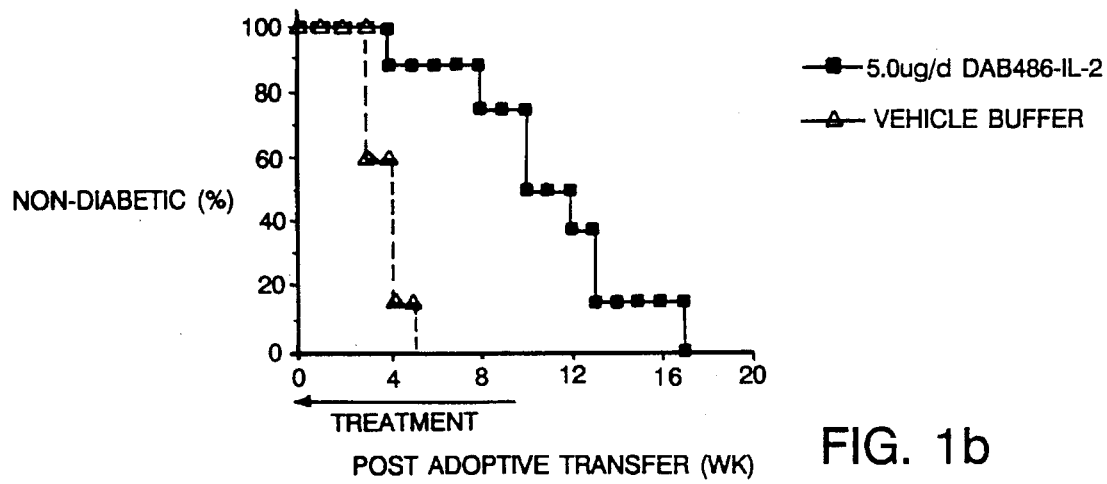
Figure 2:
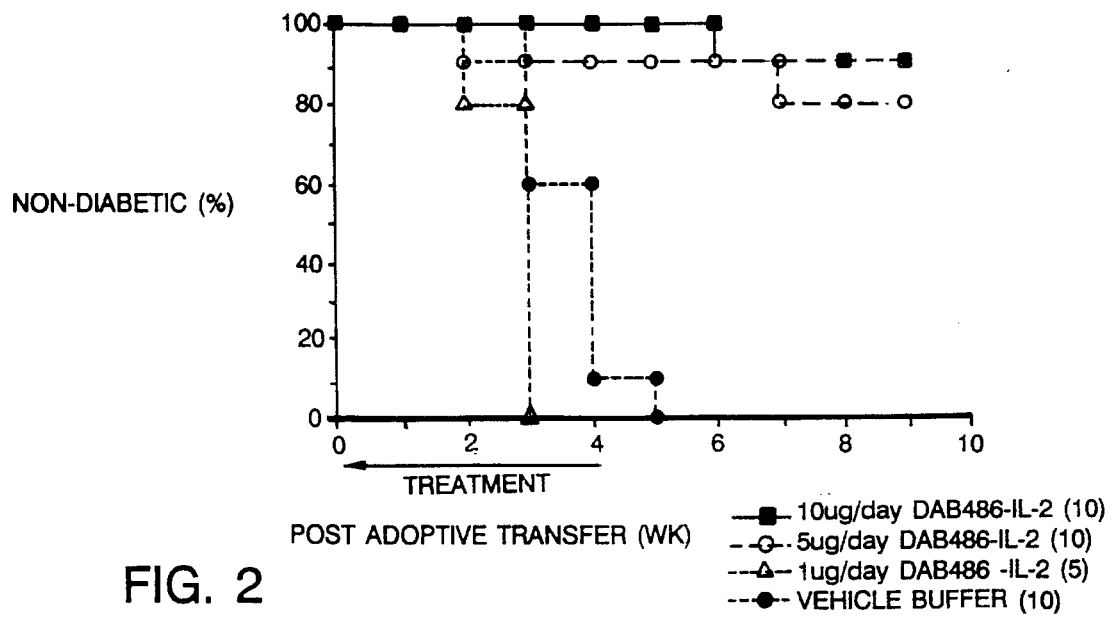
FIG. 2 is a graphical representation of the effect of $DAB_{486}IL$-2 on the acquisition of diabetes. Prediabetic NOD mice were irradiated (1,000 rad) and injected i.v. with $2 \times 10^7$ mononuclear spleen cells from a diabetic mouse. Mice were treated with vehicle buffer (TBS), 10, 5 or 1 μg/day of $DAB_{486}IL$-2.

A third set of experiments was designed to determine whether mice treated for 4 weeks with 5 µg/d $DAB_{486}IL$-2 would remain permanently free of IDDM. Although the rate of development of diabetes was markedly delayed in $DAB_{486}IL$-2 treated mice, the 8 treated mice eventually became diabetic between 8 and 16 weeks after adoptive transfer of diabetogenic cells. All control mice became diabetic by 5 weeks after adoptive transfer (FIG. 1b). Of interest, the level of blood glucose in the $DAB_{486}IL$-2 treated mice that eventually became diabetic was always lower than untreated mice. For example, at the onset of IDDM, untreated mice had blood glucose levels of 274±8 mg/dl, while treated mice had values of 231±10 mg/dl ($p<0.01$). Blood glucose levels continued to increase in untreated mice and the majority of this group achieved values above 300 mg/dl, while mice receiving either 10 or 5 µg/d $DAB_{486}IL$-2 never exhibited values as high as 300 mg/dl. Thus, even though mice treated with 4 weeks of $DAB_{486}IL$-2 eventually did become diabetic, treatment with this fusion-toxin dampened the severity and rate of progression of disease.

Mice treated with IL-2 alone had a similar incidence of diabetes (7/8) as compared to the vehicle control group (5/5), and mice injected with $DA(197)B_{486}IL$-2 (5/8) also became diabetic (Table 1). Thus, IL-2 alone or $DA(197)B_{486}IL$-2 could not account for the beneficial action of $DAB_{486}IL$-2.

TABLE 1

IL-2 DOES NOT ALTER THE TEMPO
OF DIABETES IN NOD MICE

| TREATMENT | INCIDENCE OF DIABETES* (%) |
|---|---|
| IL-2 (2.5 µg/d) n = 8 | 88 |
| $DA(197)B_{486}IL$-2(10 µg/d) n = 8 | 63 |
| VEHICLE BUFFER N = 5 | 100 |

*Blood glucose determination at 3 weeks after adoptive transfer of prediabetic NOD mice irradiated (1000 rad) and injected i.v. with $2 \times 10^7$ spleen cells from diabetic NOD mice. Subcutaneous treatments were given daily in a volume of 0.1 ml.

TABLE 2

PRETREATMENT OF DIABETIC NOD MICE
WITH DAB486-IL-2 PROTECTS
FROM ADOPTIVE TRANSFER OF DIABETES

| PRETREATMENT OF DONORS | ONSET OF DIABETES (weeks after adoptive transfer) |
|---|---|
| none+ n = 9 | 3, 3, 3, 4, 4, 5, 5, 8 |
| $DAB_{486}IL$-2 (10 µg/d)* n = 4 | 8, 14, >16, >16 ($p<0.01$) |

+Young NOD mice were irradiated (1,000 rad) and reconstituted with $2 \times 10^7$ mononuclear spleen cells from recently diabetic untreated NOD mice and received no further treatment.
*Young NOD mice were irradiated (1,000 rad) and reconstituted with $2 \times 10^7$ mononuclear spleen cells from recently diabetic NOD mice that were treated with $DAB_{486}IL$-2 (10 µg/day) for one week and received no further treatment.

Therapy

Generally, the molecules of the invention can be administered by intravenous infusion/injection. They may also be administered subcutaneously or intramuscularly. Dosages of molecules useful in the methods of the invention will vary, depending on factors such as the age of the patient, the severity of diabetes in the patient and the route of administration. Patients may be treated with 25 to 300 kU/kg of either $DAB_{486}IL$-2 or $DAB_{389}IL$-2. Either compound can be administered to a patient daily, or intermittently, or daily for a period of time, followed by intermittent administration.

More than 100 patients have received $DAB_{486}IL$-2 in Phase I/II clinical protocols. The molecule is well tolerated with the maximum tolerated dose (MTD) established by transient asymptomatic hepatic transaminase elevations in about 30% of patients treated at the MTD. Anti-tumor effects have been seen in approximately 40% of patients; responses were noted in B-cell leukemias and lymphomas, cutaneous T-cell lymphoma and Hodgkin's disease (LeMaistre et al., Blood 360a:abstract 1429, 1990; Woodworth et al., Fourth International Conference on Human Retrovirology, 1991). Serum concentrations of $10^{-8}M$ $DAB_{486}IL$-2 have been safely achieved in patients with IL-2 receptor expressing malignancies. Significant anti-tumor effects have been observed in highly refractory leukemia/lymphoma patients and these effects have occurred despite the presence of elevated soluble IL-2R levels in all patients. This observation is consistent with data which suggest that soluble IL-2R does not interfere with binding of IL-2 to the high affinity interleukin-2 receptor. Animal and human studies have demonstrated that $DAB_{486}IL$-2 has no general immunosuppressive effect (LeMaistre et al., supra; Woodworth et al., supra).

Experiments indicate that binding and internalization of $DAB_{486}IL$-2 by cells bearing the high affinity IL-2 receptor occurs within 30 minutes of exposure, resulting in maximal inhibition of protein synthesis within several hours. Therefore, the molecule should be effective even if the serum half-life is rather short.

Clinical Studies in Patients with IDDM

A phase I/II study of safety, tolerability, pharmacokinetics and biological response of $DAB_{486}IL$-2 in humans with recent onset IDDM is underway.

This pilot study was designed to evaluate the safety and tolerability of $DAB_{486}$-2 in IDDM patients and to assess pharmacokinetics and immune function effects, together with changes in diabetic status as determined by insulin requirement, C-peptide levels, and control of hyperglycemia. Based on experience in similar studies, such effects can be preliminarily assessed over a 4 to 6 week period following agent administration, and thus, onset autoimmune diabetes mellitus provides a clinical model for the evaluation of potential immunologic and anti-diabetic effects of a new therapeutic like $DAB_{486}IL$-2.

$DAB_{486}IL$-2 has been administered to individuals over 15 years of age with symptoms ≤4 months in duration, HLA DR3 or 4 and/or anti-islet cell antibody formation. Patients received a 60 minute intravenous infusion daily for 7 days in a cohort dose-escalation protocol, evaluating dose levels of 0.025, 0.05, and 0,075 mg/kg. This pilot study has evaluated 24 patients, each receiving a single course.

To date, 18 patients are evaluable. The agent has been well tolerated in this group of patients; there has been mild transient hepatic transaminase elevations in 15 to 20% of patients, two transient episodes of edema and two incidences of mild rash suggestive of hypersensitivity-like effects. Surprisingly, 8 of these patients (3 in the 0.025 mg/kg, 3 in the 0.05 mg/kg, and 2 in the 0.075 mg/kg dose groups) have had a substantial decrease in insulin requirement, together with a sustained increase in C-peptide (≧0.6 nanomolar), and a normalization of glycosylated hemoglobin. Data analysis for the other 6 patients is underway.

Further, in these responding patients, the addition of cyclosporin A at a non-nephrotoxic dose (4–5 mg/kg/d) resulted in sustained or even greater improvement in the response parameters. Since this low dose of cyclosporin A would not be expected to induce such an improvement (Bach, 1989 in Thompson, ed. Cyclosporin A: Mode of Action and Clinical Applications. London Kleuver Academic Publishers, 181), this observation suggests that treatment of diabetic patients with an IL-2 fusion toxin such as $DAB_{486}$IL-2 followed by, or in conjunction with, low dose cyclosporin A is a highly effective way to safely administer cyclosporin A to patients with diabetes.

The data described above demonstrate that $DAB_{486}$IL-2 is capable of suppressing IDDM in NOD mice, and that this suppression can be attributed to the ability of $DAB_{486}$IL-2 to target IL-2 expressing T cells and kill them. The data described above also demonstrate that $DAB_{486}$IL-2 is surprisingly useful in reducing insulin dependence in human patients that already have IDDM.

What is claimed is:

1. A method of treating a patient with diabetes, said method comprising administering to said patient a hybrid molecule comprising a first portion and a second portion joined together covalently, said first portion comprising a cytotoxin capable of decreasing cell viability, said second portion comprising all or an interleukin-2 receptor binding portion of interleukin-2 capable of binding to a high affinity interleukin-2 receptor on a cell, said hybrid molecule being administered to said patient in the presence or absence of cyclosporin A administered at a non-nephrotoxic dosage of 4–5 mg/kg/day until said patient's diabetic condition has substantially improved, following which cyclosporin A, but not said hybrid molecule is administered to said patient, said cyclosporin A being administered at a non-nephrotixic dosage of 4–5 mg/kg/day.

2. The method of claim 1, wherein said hybrid molecule kills cells bearing said receptor.

3. The method of claim 1, wherein said cytotoxin is a fragment of a peptide toxin which is enzymatically active but which does not possess generalized eukaryotic receptor binding activity.

4. The method of claim 1, wherein said cytotoxin comprises fragment A of diphtheria toxin and enough of fragment B of diphtheria toxin to form a pore in a cell membrane.

5. The method of claim 1, wherein said hybrid molecule is $DAB_{486}$IL-2.

6. The method of claim 5, wherein said $DAB_{486}$IL-2 is administered at a dosage of 25 to 300 kU/kg.

7. The method of claim 1, wherein said hybrid molecule, is $DAB_{389}$IL-2.

8. The method of claim 7, wherein said $DAB_{389}$IL-2 is administered at a dosage of 25 to 300 kU/kg.

9. The method of claim 1, wherein said patient is not dependent upon the administration of exogenous insulin.

10. The method of claim 1, wherein said patient has antibodies to insulin.

11. The method of claim 1, wherein said patient has antibodies to islet cells.

12. The method of claim 1, wherein said patient is dependent upon the administration of exogenous insulin.

13. The method of claim 1, wherein administration of said hybrid molecule is stopped prior to administration of said cyclosporin A.

14. The method of claim 1 wherein administration of said hybrid molecule occurs in the absence of cyclosporin A administration.

* * * * *